United States Patent [19]

Kühl et al.

[11] 4,140,121
[45] Feb. 20, 1979

[54] IMPLANTABLE DOSING DEVICE

[75] Inventors: Dieter Kühl, Möhrendorf; Günter Luft, Lauf a.d. Pegnitz; Konrad Mund, Erlangen; Gerhard Richter, Erlangen; Ferdinand V. Sturm, Erlangen, all of Fed. Rep. of Germany

[73] Assignee: Siemens Aktiengesellschaft, Berlin and Munich, Fed. Rep. of Germany

[21] Appl. No.: 802,969

[22] Filed: Jun. 2, 1977

[30] Foreign Application Priority Data

Jun. 11, 1976 [DE] Fed. Rep. of Germany ....... 2626294

[51] Int. Cl.² .............................................. A61M 31/00
[52] U.S. Cl. .................................... 128/260; 128/213; 128/272; 424/19
[58] Field of Search ............... 128/130, 213, 272, 260; 424/19, 228

[56] References Cited

U.S. PATENT DOCUMENTS

| 3,896,806 | 7/1975 | Wichterle | 424/19 |
| 3,987,790 | 10/1976 | Eckenhoff et al. | 128/130 |
| 4,003,379 | 1/1977 | Ellinwood | 128/260 |
| 4,016,880 | 4/1977 | Theeuwes et al. | 128/260 |
| 4,034,756 | 7/1977 | Higuchi et al. | 128/260 |

Primary Examiner—Leland A. Sebastian
Attorney, Agent, or Firm—Kenyon & Kenyon, Reilly, Carr & Chapin

[57] ABSTRACT

The invention relates to an implantable dosing device for the continuous, controllable release of medication in the human or animal body, comprising a medicine reservoir of variable volume and a liquid chamber which is tensionally connected to the medicine reservoir and the volume of which can be varied by liquid which is transported through an ion exchange diaphragm by electro-osmosis due to an electric field between two electrodes. According to the invention, the electrodes in such an implantable dosing device are hydrogen electrodes which are connected to each other by a line for hydrogen, and means are further provided for compensating hydrogen losses.

9 Claims, 4 Drawing Figures

IMPLANTABLE DOSING DEVICE

BACKGROUND OF THE INVENTION

The invention relates to an implantable dosing device for the continuous, controllable release of medication in the human or animal body, comprising a medicine reservoir of variable volume and a liquid chamber which is tensionally connected to the medicine reservoir and the volume of which can be varied by liquid which is transported through an ion exchange diaphragm by electro-osmosis due to an electric field between two electrodes.

In a number of diseases it is necessary for patients to receive medication over extended periods of time. Examples of this are the administration of Insulin in the case of diabetes, corticosteroids in the case of rheumatic diseases or cytostatica in the case of cancer. These medicines have heretofore been delivered to the body of the patient predominantly either orally or by injection at certain time intervals. Such delivery of medication is therefore intermittent and is matched to the actual requirement of the patient only imperfectly. With many medicines the accurate dosage is, furthermore, very important, as excess as well as deficiency may have detrimental effects.

A number of devices have therefore been developed for delivering medication to the human or animal body, in order to permit better, more accurate dosing. The following systems in particular, are known:
mechanical pumps;
pumping systems, in which a volume change is brought about by changing the state of a gas (decompression) or a liquid (evaporation);
pump systems, in which an osmotic pressure difference is utilized for the transport;
pumping systems, in which a volume is changed by electro-osmosis.

The main disadvantage of the first-named systems is that movable parts must be used, for example, gears and valves, which are subject to wear in operation and in most cases do not meet the requirements specified as to dosing accuracy, service life and tightness. These pumping systems have the further disadvantage that a relatively large amount of energy is required for their operation. While continuous release can be achieved by utilizing an osmotic pressure difference for transporting small volumes of medication, uniform release cannot be achieved thereby. In addition, an osmosis pump cannot be controlled without a suitable control valve.

For the continuous, controllable or regulated delivery of medicines to the human or animal body, a dosing device is also known which works according to the principle of electro-osmosis and comprises a medicine reservoir provided with an opening as well as means for varying the reservoir volume in the form of a liquid chamber of variable volume, which is tensionally connected to the medicine reservoir (German Offenlegungsschrift No. 2 239 432 or U.S. Pat. No. 3,894,538). The volume change of this chamber is preferably brought about by the penetration of liquid by electro-osmosis due to an electric field. For this purpose, two porous electrodes are provided, between which an ion exchange diaphragm is arranged.

Such a dosing device, which works by electro-osmosis, has the advantage that it requires neither mechanically movable parts nor valves, and operates perfectly quiet; in addition, it can be accommodated in a small volume and relatively little energy is required to pump small amounts of medication. The dosing device is therefore highly suited for implantation in the body of patients.

The electrodes of the known dosing devices can be supplied with external power, for example, from a battery. Platinum electrodes, in particular, are used for this purpose. However, such electrodes can be operated with only small currents since otherwise the water decomposition which takes place due to electrolysis leads to gas development. This is because the occurring reaction products diffuse off too slowly and can no longer be removed. It is also known to design the electrodes themselves to deliver current. For this purpose, zinc, cadmium or aluminum anodes and silver/silver chloride cathodes, for example, can be used. Such electrodes have the disadvantage, however, that they are consumed and therefore limit the length of operation of the electro-osmosis dosing device.

Instead of consumable electrodes, one can also use electrodes which are operated with substances of the body itself, in particular, glucose anodes and oxygen cathodes. With such electrode systems, current densities of about 1 to 5 $\mu A/cm^2$ can be achieved at present. However, as with the currently available ion exchange diaphragms, current densities of about 0.2 $mA/cm^2$ are required for the transport of liquid. Thus, the electrodes would be required to have, for example, an area of about 55 $cm^2$ in order to generate a current of 110 $\mu A$ which is required for transporting 2 $\mu l$/hour. Electrodes of this size are hardly suitable for implantation, however. In addition, the current generation with the mentioned electrodes is dependent on the supply of glucose and oxygen. Particularly if the active areas of the electrodes are limited by the growth of connective tissue, the danger therefore exists that the attainable currents and the dosing capacity of the electro-osmosis pump may become still smaller.

SUMMARY OF THE INVENTION

It is accordingly an object of this invention to develop an implantable dosing device of the aforementioned type in such a manner that the current required for the release of the medication is available over extended periods of time and in sufficient quantity.

According to the invention, this is achieved by the provision that the electrodes are hydrogen electrodes; that the hydrogen electrodes are connected to each other by a line for hydrogen; and that means for compensating hydrogen losses are provided.

The dosing device according to the invention makes possible not only the continuous, uniform, controllable or regulated release of medication, also in small amounts, to the human or animal organism while consuming little energy, but it additionally ensures that this dosing of medicine also takes place over an extended period of time accurately and without disturbance, i.e., the dosing device has a long operating time. This is essentially due to the fact that the hydrogen is conducted between the hydrogen electrodes so to speak, in a closed loop.

Medication is understood in the context of the present Patent Application to mean in the broadest sense all substances which serve in any way to improve, restore or maintain a patient's health, for instance, also hormones, enzymes and vitamins.

In the operation of the dosing device according to the invention, which is also called an electro-osmosis pump, hydrogen is developed at one of the electrodes, the cathode. This hydrogen is fed through the hydrogen line to the other electrode, i.e., the anode, and is consumed there. In long-term operation, certain losses of hydrogen cannot be avoided which occur, both through gas saturation of the liquid in the dosing device and by out-diffusion of the hydrogen, particularly through the ion exchange diaphragm.

For compensating these hydrogen losses in the electro-osmosis osmosis pump, the following measures can advantageously be taken according to the invention. At the line between the two hydrogen electrodes, a chamber can be provided which contains a material that stores hydrogen under pressure. The material in this hydrogen reservoir is preferably a transition metal or a transition metal compound storing hydrogen, particularly $LaCo_5$. However, $LaNi_5$ and $TiFe$, for example, may also be used. The hydrogen pressure is kept constant by way of such hydrogen-storing compounds, i.e., hydrides. The hydrogen losses, however, can also be made up by developing more hydrogen at the cathode than is consumed at the anode. An auxiliary electrode is then used for this purpose. As the hydrogen losses are relatively small, only little current is required for replenishing the hydrogen. Therefore, a glucose electrode can be used as the auxiliary electrode, that is, an electrode at which the substance of the body itself, glucose, is electrochemically converted. However, the auxiliary electrode may also be a consumable anode of non-noble metal, particularly of aluminum. In these electrodes, the metal is consumed in the course of time, i.e., it is dissolved. In order to keep the oxidation products formed in this process away from the body, the metal anode must be separated from the body tissue by a diaphragm. For an operating life of about 2 years, for example, an amount of maximally 0.2 to 0.5 g/aluminium is sufficient.

In electro-osmosis, liquid is transported through the ion exchange diaphragm and the electrodes when current flows. For example, negative charges are fixed in the pore walls of the ion exchange diaphragm, and the mobile positive ions, which are necessary for reasons of electroneutrality, then travel in the electric field and take the liquid along by friction.

In dosing device according to the invention, only a single ion exchange diaphragm arranged between the two porous electrodes need be provided for the transport of the liquid. The ion exchange diaphragm is chosen and the electrodes are arranged in such a manner that the electro-osmosis transport of the liquid takes place into the liquid chamber. It is advantageous, however, to provide each of the two hydrogen electrodes with an ion exchange diaphragm on the outside and to arrange the liquid chamber at least partially between the two electrodes. Here too, the electrodes are made porous in order to allow the passage of the liquid. Such an arrangement has the advantage that it is very effective, since ions together with their hydrate shell travel through both electrodes. In the dosing device according to the invention, the two hydrogen electrodes are furthermore provided advantageously on the side facing away from the ion exchange diaphragm with a layer of asbestos paper at least partially covering it, i.e., an asbestos diaphragm, in order to prevent the passage of gas. The electrodes may be embedded, however, also in a solid housing and be provided only with a discharge for the liquid passing through due to the electro-osmosis.

The medicine is ejected from the medicine reservoir in the dosing device according to the invention by means of the volume change of the liquid chamber which is tensionally connected to the medicine reservoir. For this purpose, the medicine reservoir is made at least in part of elastic material and care is taken that the volume change of the liquid chamber is converted into a compression force onto the elastic material. For this purpose the dosing device preferably has a housing, the interior of which is divided by an elastic partition into two chambers, of which one constitutes the liquid chamber and the other the medicine reservoir. The latter is provided with a discharge opening which is advantageously closed by a plug with fine pores in order to prevent back diffusion of body fluid into the medicine reservoir or an uncontrolled discharge of the medicine from the reservoir. For transporting the medicine or for transporting the liquid by electro-osmosis, the two hydrogen electrodes are connected to a power supply, for example, a battery. The magnitude of the current feeding the electrodes can be varied here and the transported amount of medication is proportional to the current or the current density.

DETAILED DESCRIPTION OF THE INVENTION

Figure 1:
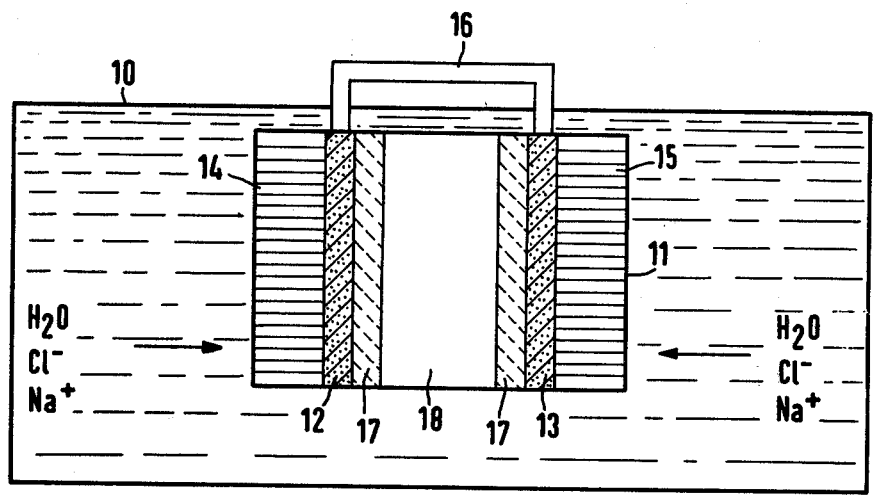
FIG. 1 shows the basic design of an electro-osmosis pump according to the invention, FIG. 2, a preferred embodiment of the dosing device according to the invention.

In FIG. 1, the basic design of the electro-osmosis pump is shown schematically. Vessel 10 filled with physiological saline solution (NaCl) is provided an electro-osmosis cell 11. The cell 11 contains two hydrogen electrodes, an anode 12 and a cathode 13. Both electrodes consist preferably of platinum sponge bonded with polytetrafluoro ethylene, however other porous noble-metal electrodes such as screen or film electrodes can also be used. Ion exchange diaphragms are provided in front of both electrodes. An anion exchange diaphragm 14 is arranged in front of the anode 12 and a cation exchange diaphragm 15 in front of the cathode 13. The two hydrogen electrodes 12 and 13 are connected to each other via a gas line 16 for hydrogen. Before starting up, the two electrodes and the gas line are filled with hydrogen under a pressure of 1.1 to 2.0 × $10^5$ N/m² and preferably, 1.2 to 1.3 × $10^5$ N/m². The electrodes 12 and 13 are connected to each other via an external circuit, not shown in FIG. 1. On the inside of both electrodes is attached asbestos paper 17, which is gastight but not liquid-tight, so that no liquid can collect at the electrodes if the gas pressure is sufficiently high.

During the operation of the electro-osmosis cell, the electrochemical reaction of the hydrogen takes place at the electrodes. At the anode 12 the hydrogen is dissolved: $H_2 \rightarrow 2H^+ + 2e^-$. As almost exclusively anions are transported through the anion exchange diaphragm 14, which is in front of the electrode 12, assuming low electrolyte concentration, $Cl^-$ ions including hydrate shell are transported to the electrode for charge neutralization. Thus, an HCl solution then passes through the electrode 12 and the asbestos paper 17 into a liquid chamber 18. Hydrogen precipitation takes place at the cathode 13: $2 H_2O + 2e^- \rightarrow 2 OH^- + H_2$. As almost exclusively cations are transported through the cation exchange diaphragm 15 which is in front of the electrode 13, Na$^+$ ions with hydrate shell are transported to the cathode 13. Thus, an NaOH solution gets into the liquid chamber 18 via the cathode and the asbestos paper 17.

Accordingly, the same amount of hydrogen gas is developed at the cathode 13 as is consumed at the anode 12. In this process, equal equivalents of Cl$^-$ and Na$^+$ ions are transported through the two ion exchange diaphragms. The hydrochloric acid (HCl) formed at the anode is neutralized in the liquid chamber 18 by the caustic soda solution (NaOH) formed at the cathode, so that ultimately, a diluted sodium chloride solution is transported. The hydrogen used for the transport is thereby circulated in a closed loop. The volume increase in the liquid chamber 18, as it is tensionally connected to a medicine reservoir, then causes medication to be ejected from this reservoir.

Figure 2:
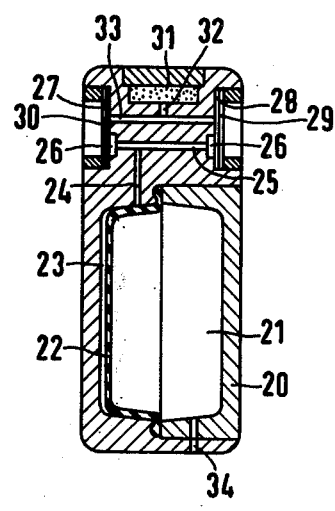

In FIG. 2, a preferred embodiment of the dosing device according to the invention is shown. Housing 20, which consists preferably of epoxy resin, contains a medicine reservoir 21 which is separated from a liquid chamber 23 by a movable diaphragm 22 of silastic rubber and contains, for example, an Insulin solution. The liquid chamber 23 is filled with liquid, preferably with a physiological saline solution. The diaphragm 22 may advantageously be coated, as may be the medicine reservoir 21, with metal. There by, increased tightness is achieved and chemical reactions of the medication with the diaphragm material or the material of the medicine reservoir can be prevented. By way of lines 24 and 25, which themselves are likewise part of this chamber and are therefore also filled with liquid, the liquid chamber 23 adjoins asbestos diaphragms 26 which in part cover the anode 27 and the cathode 28, respectively; the remaining portion of the two electrodes is essentially covered up by the material of the housing. The cathode and the anode are arranged, as shown in FIG. 2, on opposite sides in respective recesses in the housing 20 and are fastened therein in a suitable manner. On the side facing away from the asbestos diaphragm 26, cathode 28 is covered up by a cation exchange diaphragm 29, and the anode 27 by an anion exchange diaphragm 30.

In the operation of the dosing device, Na$^+$ and Cl$^-$ ions (including the hydrate shell) travel from the body fluid through the ion exchange diaphragms 29 and 30. The two ion exchange diaphragms are advantageously covered up toward the body with tissue-compatible, liquid-permeable material such as hydrogels. There is further provided within the housing 20 a chamber 31 for hydrogen storage, which contains a metal hydride. The hydrogen storage chamber 31 is connected via line 32 to a hydrogen line 33 which connects the two electrodes 27 and 28 with each other. Instead of the hydrogen storage chamber, an auxiliary electrode may also be provided, under the influence of which additional hydrogen is developed at the cathode 28. The medication contained in the medicine reservoir 21 leaves the dosing device via the opening 34. The means for the power supply and current regulation are not shown in FIG. 2.

Figure 3:
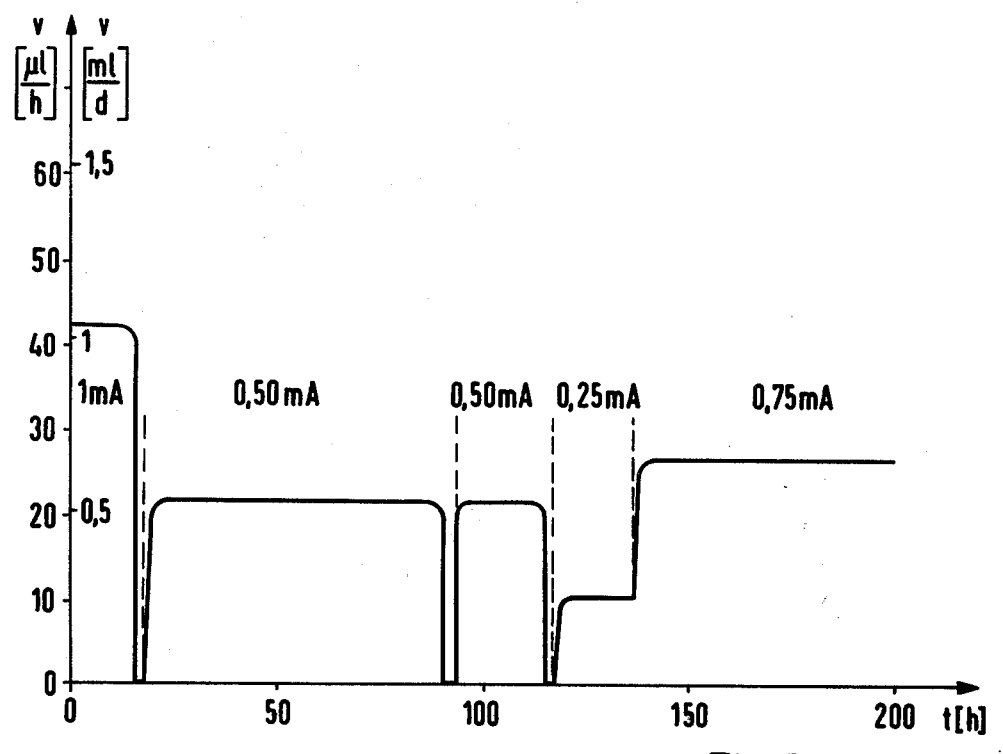
FIGS. 3 and 4 show the control behavior of different embodiments of the dosing device according to the invention.

FIG. 3 shows the control behavior of such an electro-osmosis pump, which has two electrodes of platinum sponge. The transported quantity v in $\mu$l/hr. (or ml/day) is plotted here on the ordinate and the time t in hours on the abscissa. The ion exchange diaphragms had an area of 4 cm$^2$ and the hydrogen pressure was $1.2 \times 10^5$ N/m$^2$.

The transported amount can be adjusted, as is seen in FIG. 3, by changing the current. With a transported amount of 0.5 ml/day, the power consumption is about 400 $\mu$W. The time constant of the regulation is about 20 to 30 minutes and in continuous operation, a small deviation of about $\pm 3$ to 4% occurs. For compensating the hydrogen losses, there was provided in the storage chamber of the dosing device 1 g of a hydride which was prepared from the alloy LaCo$_5$ by saturation with hydrogen in an autoclave under pressure.

Figure 4:
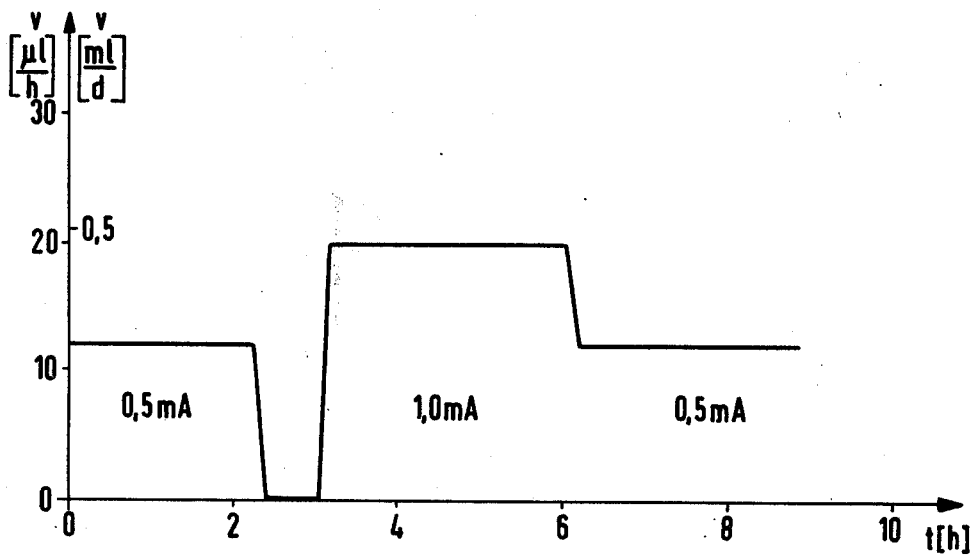

In FIG. 4, the control behavior of an electro-osmosis pump is similarly shown, in which the area of the ion exchange diaphragms was 0.7 cm$^2$; the hydrogen pressure was about $1.3 \times 10^5$ N/m$^2$. The power required for such a dosing device was about 500 $\mu$W with a transport capacity of 0.25 ml/day. The time constant of the regulation is about 5 minutes and at most only a minor deviation of the transport of about $\pm 1$ to 2% occurs during continuous operation. An auxiliary anode of aluminum serves for compensating the hydrogen losses. This auxiliary anode was intermittently switched on and off as a function of the gas pressure in the hydrogen line via a miniature mercury manometer. The average load of the auxiliary electrode was 30 $\mu$A.

What is claimed is:

1. In an implantable dosing device for the continuous, controllable release of medication in the human or animal body comprised of a medication reservoir of variable volume, a liquid chamber tensionally connected to said medication reservoir, and volume varying means comprised of an ion-exchange diaphragm interposed between two electrodes whereby liquid is transported in an electro-osmotic manner due to an electric field between said electrodes, the improvement wherein said electrodes are hydrogen electrodes connected to each other by way of a line for hydrogen, and wherein said dosing device further includes means for compensating hydrogen losses.

2. An implantable dosing device according to claim 1, wherein said means for compensating hydrogen losses comprises a chamber containing material storing hydrogen under pressure provided at the hydrogen line.

3. An implantable dosing device according to claim 2, wherein said chamber in the hydrogen line contains a transition metal or a transition metal compound storing hydrogen.

4. An implantable dosing device according to claim 3 wherein said transition metal compound is LaCo$_5$.

5. An implanatable dosing device according to claim 1, wherein said means for compensating hydrogen losses comprises an auxiliary electrode.

6. An implantable dosing device according to claim 5, wherein said auxiliary electrode is a glucose electrode.

7. An implantable dosing device according to claim 5, wherein said auxiliary electrode is a consumable metallic electrode.

8. An implantable dosing device according to claim 1 wherein each of the two hydrogen electrodes is provided with an ion exchange diaphragm on the outside thereof and said liquid chamber is arranged at least in part between the two hydrogen electrodes.

9. An implantable dosing device according to claim 8, wherein the hydrogen electrodes are covered, at least in part, with a layer of asbestos paper on the side facing away from said ion exchange diaphragm.

* * * * *